(12) United States Patent
Ueda et al.

(10) Patent No.: US 10,046,153 B2
(45) Date of Patent: Aug. 14, 2018

(54) CONNECTOR

(71) Applicant: TERUMO KABUSHIKI KAISHA, Shibuya-ku, Tokyo (JP)

(72) Inventors: Yasuhiro Ueda, Kofu (JP); Tsukasa Takahashi, Musashino (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 434 days.

(21) Appl. No.: 14/666,931

(22) Filed: Mar. 24, 2015

(65) Prior Publication Data
US 2015/0190623 A1 Jul. 9, 2015

Related U.S. Application Data

(63) Continuation of application No. PCT/JP2012/075039, filed on Sep. 28, 2012.

(51) Int. Cl.
*A61M 25/16* (2006.01)
*A61M 39/04* (2006.01)
(Continued)

(52) U.S. Cl.
CPC .......... *A61M 39/045* (2013.01); *A61M 39/10* (2013.01); *A61M 39/1011* (2013.01); *A61M 39/26* (2013.01); *F16L 37/38* (2013.01)

(58) Field of Classification Search
CPC .. A61M 39/10; A61M 39/1011; A61M 39/26; A61M 39/045
(Continued)

(56) References Cited

U.S. PATENT DOCUMENTS 5,466,219 A 11/1995 Lynn et al.
6,569,117 B1 5/2003 Ziv et al.
(Continued)

FOREIGN PATENT DOCUMENTS

EP 1 829 579 A1 9/2007
JP 2006-223587 A 8/2006
(Continued)

OTHER PUBLICATIONS

The extended European Search Report dated May 9, 2016, by the European Patent Office in corresponding European Patent Application No. 12885329.8-1662. (7 pages).
(Continued)

*Primary Examiner* — Kami A Bosworth
*Assistant Examiner* — Leah Swanson
(74) *Attorney, Agent, or Firm* — Buchanan Ingersoll & Rooney PC

(57) ABSTRACT

A connector includes in a main body, first to third ports each having a flow channel allowing inflow or outflow of an infusion solution, an internal flow channel configured to communicate between flow channels of the first port and the second port, and a through hole connected to an internal flow channel. In the internal flow channel, an upstream side wall surface is provided which guides infusion solution flowing into the internal flow channel from the first port to the through hole, and reduces the cross-sectional area of the flow channel for the infusion solution near the through hole relative to the cross-sectional area of the flow channel of the first port in order to increase a flow rate of the infusion solution.

15 Claims, 7 Drawing Sheets

(51) Int. Cl.
*A61M 39/10* (2006.01)
*A61M 39/26* (2006.01)
*F16L 37/38* (2006.01)

(58) Field of Classification Search
USPC .......................................................... 604/537
See application file for complete search history.

(56) References Cited

U.S. PATENT DOCUMENTS

| | | | |
|---|---|---|---|
| 2007/0232989 | A1 | 10/2007 | Kitani et al. |
| 2007/0255202 | A1* | 11/2007 | Kitani ................. A61M 39/045 604/82 |
| 2008/0086097 | A1 | 4/2008 | Rasmussen et al. |

FOREIGN PATENT DOCUMENTS

| | | |
|---|---|---|
| JP | 2007-229392 A | 9/2007 |
| JP | 2009-195720 A | 9/2009 |
| JP | 2010-505551 A | 2/2010 |
| WO | WO 2000/040291 A1 | 7/2000 |
| WO | WO 2008/043069 A2 | 4/2008 |

OTHER PUBLICATIONS

Japanese Official Action dated Sep. 8, 2015, by the Japan Patent Office, in corresponding Japanese Patent Application No. 2014-537988 with English translation (9 pages).

International Search Report (PCT/ISA/210) dated Dec. 25, 2012 by the Japanese Patent Office as the International Searching Authority for International Application No. PCT/JP2012/075039.

Japanese Office Action (Notification of Reasons for Refusal) dated Feb. 14, 2017, by the Japanese Patent Office in corresponding Japanese Patent Application No. 2016-052385 with English machine translation. (6 pages).

* cited by examiner

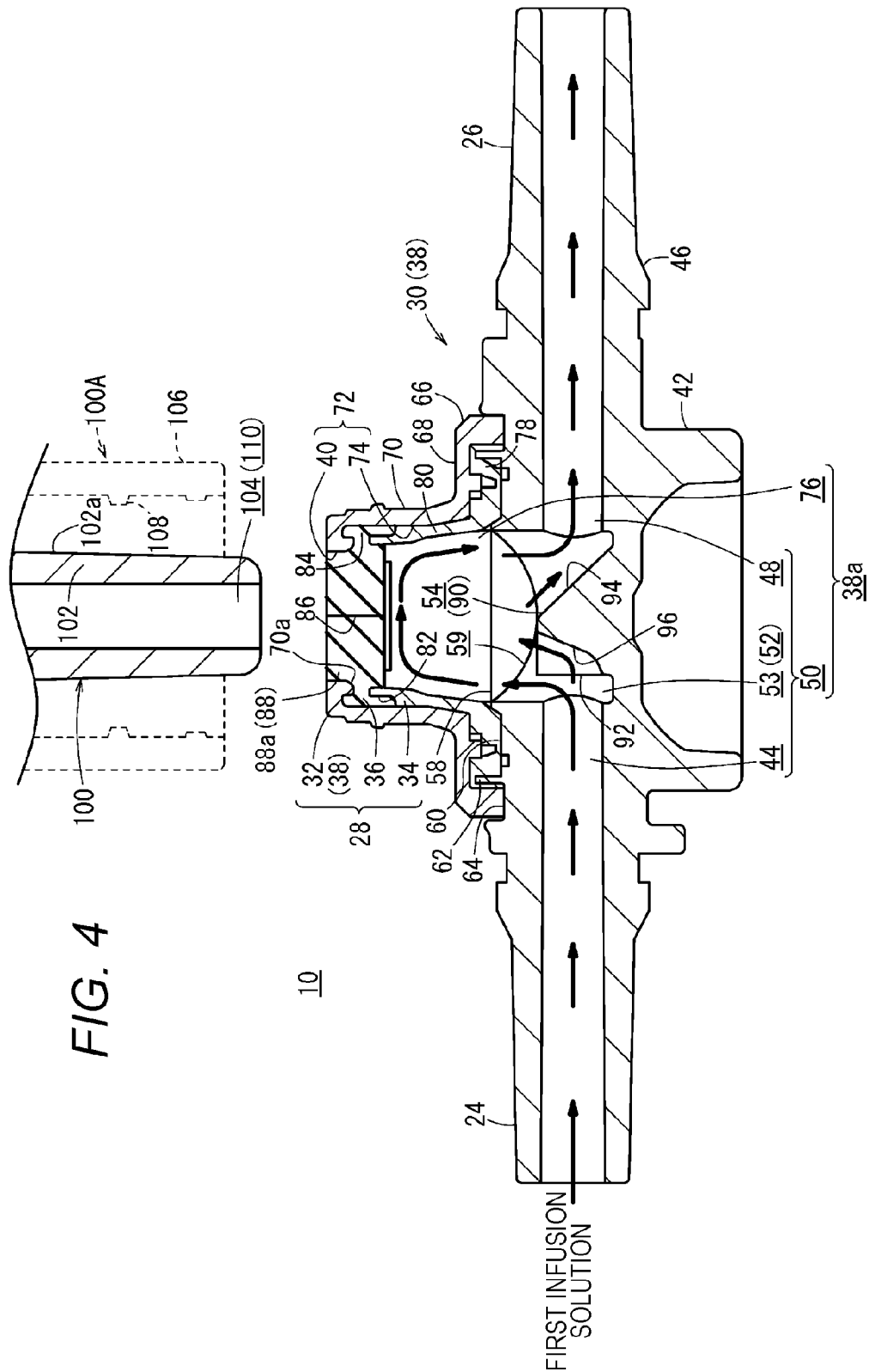

CONNECTOR

CROSS-REFERENCE TO RELATED APPLICATION

This application claims priority as a continuation application under 35 U.S.C. § 120 to International Application No. PCT/JP2012/075039 filed on Sep. 28, 2012, the entire content of which is incorporated herein by reference.

TECHNICAL FIELD

The present disclosure relates to a connector for connection of a plurality of tubes, for example, in an infusion line for infusion into a patient.

BACKGROUND DISCUSSION

Conventionally, when an infusion is performed on a patient, a plurality of tubes are connected to form an infusion line extending from an infusion bag to the patient, and the plurality of tubes are connected through a connector. Additionally, during infusion, a second infusion solution may be supplied from another (second) line to a main line which supplies a main infusion solution to the patient. The second infusion solution is mixed with the main infusion solution at the connector and then conducted to the patient. In this case, a connector including a three-way port configured to mix a plurality of infusion solutions is employed (see JP 2010-505551 W).

The connector disclosed in JP 2010-505551 W includes first and second ports configured to constitute a flow channel of a main line, and a third port configured to constitute a flow channel of another (second) line, in a main body. In the third port, a space portion connected to an internal flow channel is provided at a position branched from the internal flow channel (flow channel of the main line) and configured to communicate between the flow channels of the first and second ports. The space portion is provided for insertion and connection of a male connector of the another (second) line.

In the space portion of the third port, a fluid infusion solution (or air or the like) may become entrapped while the male connector of the another line is not connected thereto (closed state of the third port). Fluid (hereinafter also referred to as trapped fluid) trapped in such a space portion may bring about various disadvantages, particularly, in a medical device.

For example, before the infusion solution is supplied to the patient, the infusion line is filled with the infusion solution to remove air, but an air bubble (air) may be trapped in the space portion, and when the infusion solution is then supplied to the patient, the remaining air bubble may be conducted to the patient with the infusion solution. In addition, when a high nutrient solution is supplied as the infusion solution, the nutrient solution trapped in the space portion may promote the growth of bacteria in the connector, and as a result, the bacteria may be conducted into the patient. Further, when a drug solution to be supplied to the patient is changed, a next drug solution is supplied while the previous drug solution remains in the space portion, so that the different drug solutions may be mixed and conducted to the patient.

In order to overcome the above-mentioned disadvantage, there is provided a connector provided with a wall portion (fluid flow director) on an internal flow channel, for conducting the infusion solution into a space portion, in order to promote draining of any trapped fluid.

However, the wall portion provided on the internal flow channel guides the infusion solution to the space portion, with a relatively small fluid force. Therefore, the infusion solution guided to the space portion only partially influences the trapped fluid filled in the space portion, and the trapped fluid is insufficiently drained from the space portion. As a result, the trapped fluid remains in the space portion, and the same above-mentioned disadvantage may occur.

SUMMARY

An exemplary embodiment of the disclosure herein provides a connector having a simple configuration to efficiently drain fluid trapped in a space portion and thereby provide a very safe infusion to reliably supply a desired fluid.

According to one aspect of the disclosure, the connector includes a main body, first to third ports provided at the main body, each having a flow channel allowing inflow or outflow of fluid, an internal flow channel provided in the main body and configured to communicate between the flow channels of the first and second ports, a space portion provided in the third port and connected to the internal flow channel, and a wall surface provided on the internal flow channel and configured to guide fluid flowing into the internal flow channel from the first port to the space portion and to reduce the cross-sectional area of the flow channel for the fluid near the space portion relative to the cross-sectional area of the flow channel of the first port.

The connector includes the wall surface configured to guide the fluid flowing into the internal flow channel from the first port to the space portion, and to reduce the cross-sectional area of the flow channel for the fluid near the space portion relative to the cross-sectional area of the flow channel of the first port, so that a momentum of the fluid flowing from the internal flow channel to the space portion can be increased at the portion of the flow channel having the reduced cross-sectional area. That is, the fluid flowing into the internal flow channel from the first port is guided to the portion smaller than the cross-sectional area of the flow channel of the first port by the wall surface, so that the fluid is guided to the space portion with an increased flow speed. Therefore, in the space portion, the fluid having the increased momentum can promote the flow of the trapped fluid, and the trapped fluid can be readily drained from the space portion. Therefore, for example, when the connector is used to form an infusion line allowing an infusion solution to flow, the infusion has considerably increased safety and the infusion solution can be reliably administered to a patient.

In this configuration, the wall surface is preferably provided at a protruding portion extending from an axial center of the internal flow channel toward the third port, so as to face the flow channel of the first port.

The connector has the wall surface facing the flow channel of the first port, so that the portion configured to reduce the cross-sectional area of the flow channel for the fluid can be readily formed on the internal flow channel, without considerably changing the shape or the like of the internal flow channel.

In addition, the wall surface preferably faces substantially perpendicularly to the axial direction of the flow channel of the first port.

More particularly, the wall surface faces substantially perpendicularly to the axial direction of the flow channel of the first port so that the wall surface can be disposed near the flow channel of the first port. Therefore, the fluid flowing out of the flow channel of the first port can be readily conducted to the space portion.

In addition, the protruding portion preferably has a notched portion connected to the wall surface which is disposed toward the axial center of the internal flow channel.

The connector has the notched portion connected to the wall surface and disposed at the axial center of the internal flow channel so that, even when the portion having a reduced cross-sectional area of the flow channel for the fluid is formed by the wall surface, the inside of a male connector and the internal flow channel can readily communicate with each other through the notched portion when the third port and the male connector are connected to each other. Therefore, even when the male connector is connected to the connector, the fluid flowing from the first port can smoothly flow to the second port.

Further, it is preferable that the protruding portion has a downstream side wall surface facing the flow channel of the second port. The downstream side wall surface is connected at the upper part of the wall surface and inclined toward the bottom surface of the flow channel of the second port.

As described above, the downstream side wall surface is inclined toward the bottom surface of the flow channel of the second port so that the fluid flowing out of the space portion is allowed to smoothly flow along the downstream side wall surface.

Further, the wall surface preferably has an upper part projecting above the formed height of the flow channel of the first port.

As described above, the upper part of the wall surface projects upward from the formed height of the flow channel of the first port so that the interval between the wall portion on the upper side of the flow channel of the first port and the wall surface is sufficiently reduced, and the cross-sectional area of the internal flow channel near the space portion can be readily reduced.

BRIEF DESCRIPTION OF DRAWINGS

The disclosure herein will become readily more apparent to those skilled in the art upon reading the following detailed description, in conjunction with the appended drawings in which:

FIG. 4 is a side cross-sectional view illustrating an unconnected state of a male connector in the connector of FIG. 2.

DETAILED DESCRIPTION

A connector according to exemplary embodiments of the present disclosure will be described below in detail based on a relationship with an infusion set to which the connector can be applied. Application of the connector is, of course, not limited to infusion sets as one skilled in the art would recognize.

Figure 1:
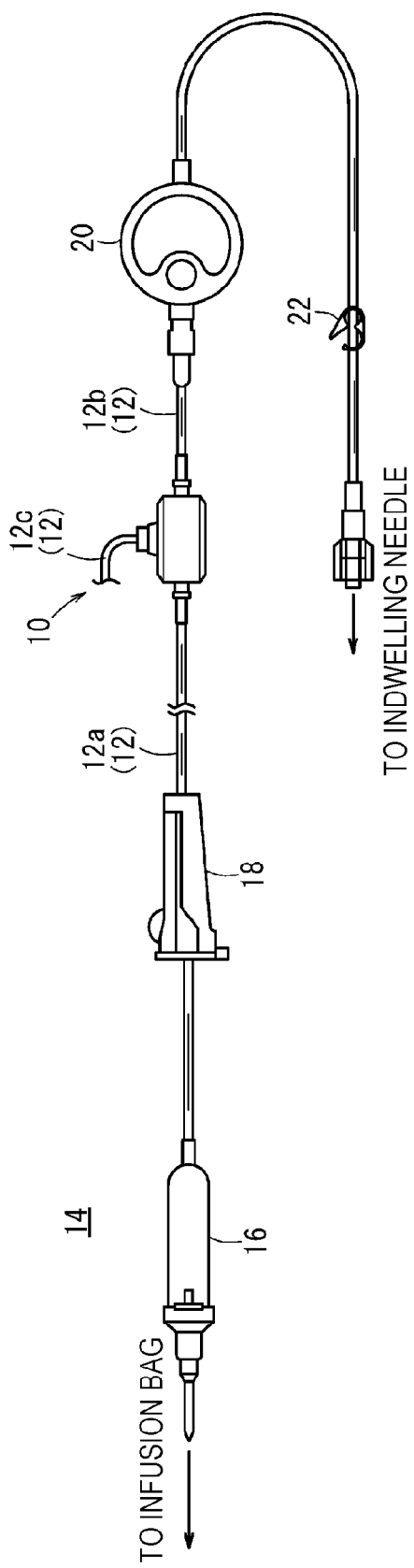
FIG. 1 is an explanatory drawing schematically illustrating an example of an infusion set to which a connector according to an exemplary embodiment of the disclosure is applied.

In an infusion line for infusion into a patient, a connector 10 functions to connect a plurality of tubes 12 to each other and is applied, for example, to an infusion set 14 as illustrated in FIG. 1. The infusion set 14 has an upstream side connected to an infusion bag (not illustrated), and a downstream side thereof is connected to an indwelling needle (not illustrated). Thus, the infusion set 14 forms the infusion line configured to administer an infusion solution from the infusion bag to the patient.

The infusion solution flowing through the infusion set 14 may include any fluid which can be administered to a living body, such as a medicinal solution, a correction electrolyte solution, or a physiological saline. Further, when the infusion solution is a medicinal solution, various medicaments may be selected, such as, for example, a sedative, an intravenous anesthetic, a narcotic analgesic, a local anesthetic, a nondepolarizing muscle relaxant, a vasopressor, an antihypertensive, a coronary vasodilator, a diuretic, an antiarrhythmic, a bronchodilator, a hemostatic agent, a vitamin preparation, an antibiotic, or fat emulsion.

The tube 12 of the infusion set 14 is provided with, for example, a drip chamber 16 configured to visually confirm the flow rate of the infusion solution supplied from an infusion bag, a pinchcock 18 configured to adjust (regulate) the flow rate of the infusion solution, an air vent filter 20 configured to exhaust air from the infusion line (or supply air into the infusion line), and a clamp 22 configured to close the tube 12. It should be understood that the infusion set 14 is of course not limited to the configuration illustrated in FIG. 1. Various members (for example, an infusion pump, a check valve, etc.) commonly disposed in an infusion line may be included in the infusion set 14 in addition to the above-mentioned members.

The tube 12 of the infusion set 14 is an elastic (flexible) tube body and constitutes a flow channel for the infusion solution. When the connector 10 is applied to the infusion set 14 described above, the connector 10 is disposed, for example, between the pinchcock 18 and the air vent filter 20. That is, the connector 10 fluidly connects a first tube 12a extending downstream from the drip chamber 16 and a second tube 12b extending upstream from the air vent filter 20 so as to allow flow therebetween and thereby constitutes a passage of a main line. The connector 10 is formed as a three port connector. Thus, a third tube 12c constituting another line (a second line) is connected to the connector 10, such that connector 10 allows communication between the main line, including the first tube 12a and the second tube 12b, and the second line.

The position of the connector 10 is not limited to the description above and can be provided at any desired position of the infusion set 14. Further, the infusion set 14 (infusion line) may be provided with not only one connector 10 but possibly a plurality of connectors 10.

Figure 2:
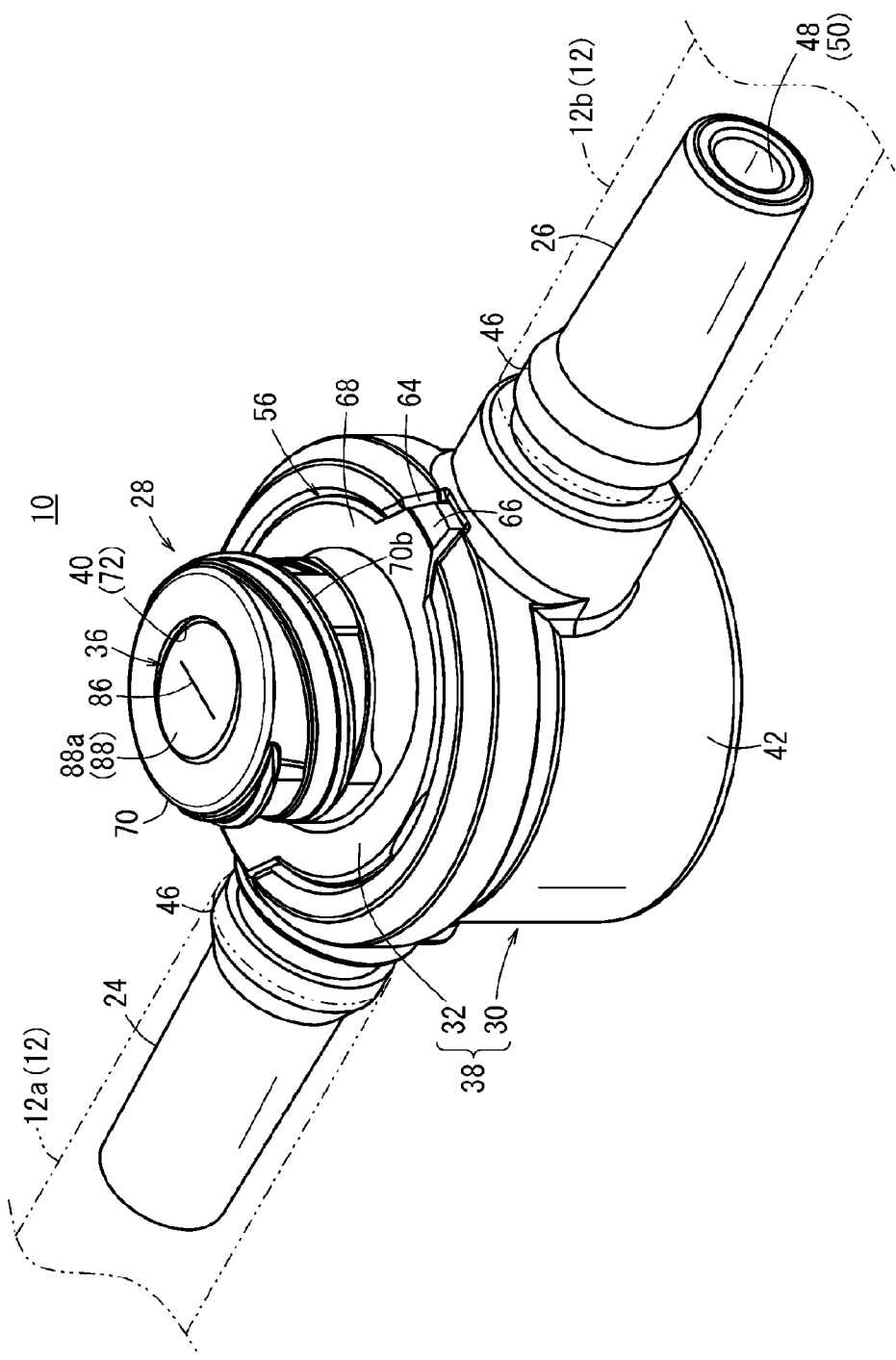
FIG. 2 is a perspective view illustrating the overall configuration of the connector of FIG. 1.

The specific configuration of the connector 10 according to an exemplary embodiment of the disclosure will be described below in detail. As illustrated in FIG. 2, the connector 10 includes a first port 24 configured to be connected to the first tube 12a constituting the main line, a second port 26 configured to be connected the second tube 12b constituting the main line, and a third port 28 configured to be connected to the third tube 12c constituting the second line (another line). The first and second ports 24 and 26 are provided on a housing 30 (shell) having an internal flow channel for the infusion solution. The third port 28 includes a cap 32 (lid), a support 34 (see FIG. 4), and a valve 36 which are separate members from the housing 30. The third port 28 is constructed by assembling these other members on the housing 30.

The housing 30 and the cap 32 are connected to each other, and thus constitute a main body 38 of the connector 10 having an internal the flow channel 38a for the infusion solution (see FIG. 4). The support 34 and the valve 36 are stored in the main body 38 and only the upper surface of the valve 36 is exposed through an opening portion 40 of the cap 32.

The housing 30, the cap 32, and the support 34 of the connector 10 are molded of a resin material in consideration of an easy molding process, reduced cost, and the like. A resin material having a higher rigidity than the tube 12 is preferably used. The resin material may be, for example, a polyolefin such as a polyethylene, a polypropylene, or an ethylene-vinyl acetate copolymer, a polyurethane, a polyamide, a polyester, a polycarbonate, a polybutadiene, or a polyvinyl chloride.

Figure 3:
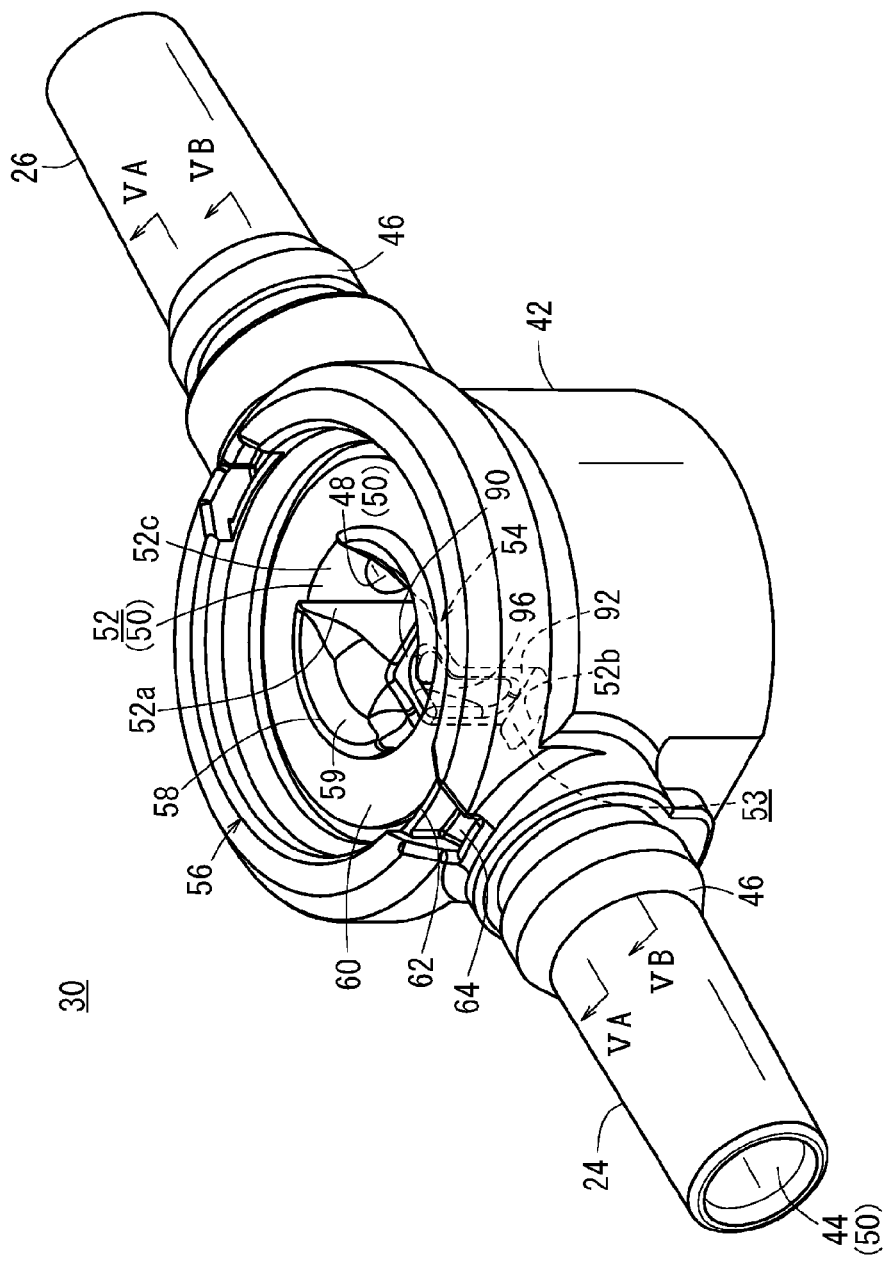
FIG. 3 is a perspective view illustrating a housing of the connector of FIG. 2.

As illustrated in FIGS. 2 and 3, the housing 30 has a bottom, cylindrical, connector base portion 42 at the center thereof, and the first and second ports 24 and 26 are connected to a side peripheral surface of the connector base portion 42. The first port 24 is formed into a substantially cylindrical shape, and linearly extends from the connector base portion 42 to the upstream side of the main line. A first port flow channel 44 configured to allow the infusion solution to flow through the first part 24 extends along an axial direction of the first port 24.

The first port 24 is configured as a male luer taper having a gradually reduced diameter extending toward an end which is inserted into the first tube 12a (lumen). Further, the first port 24 has an outer peripheral surface circumferentially formed with a projection portion 46 near the connector base portion 42. The first tube 12a is moved beyond (positioned over) the projection portion 46 such that the first tube 12a and the first port 24 are liquid-tightly connected to each other.

The second port 26 is positioned on the opposite side of the first port 24 across the connector base portion 42, and formed into the same shape as the first port 24. The second port 26 linearly extends from the connector base portion 42 to the downstream side of the main line. A second port flow channel 48 configured to allow the infusion solution to flow through the second port 26 extends along an axial direction of the second port 26. The first and second ports 24 and 26 are formed to be axially aligned, and thus, the first and second port flow channels 44 and 48 also linearly communicate with each other and their axes are coincident with each other. The connector 10 defines the linearly connected first and second port flow channels 44 and 48 as a flow channel of the main line (hereinafter, referred to as main line flow channel 50) for smooth fluidity of the first infusion solution flowing in the main line flow channel 50.

The side peripheral surface of the connector base portion 42 has a thickness large enough to connect and support the first and second ports 24 and 26. An internal flow channel 52 configured to communicate between the first port flow channel 44 and the second port flow channel 48 is formed in the connector base portion 42. The internal flow channel 52 partially constitutes the main line flow channel 50 and extends to linearly connect the main line flow channel 50. A guide wall portion 54 configured to guide the flow of the first infusion solution vertically (direction in which the cap 32 is connected) is formed at the axial center of the internal flow channel 52. The guide wall portion 54 will be described in detail later.

The connector base portion 42 has an upper side constituting a mounting portion 56 configured to mount the cap 32 and the support 34. The mounting portion 56 is formed by notching the upper surface of the connector base portion 42 into a circular shape. The mounting portion 56 includes a circular exposure opening 58 configured to expose the internal flow channel 52 at the center, a disposition portion 60 which forms a flat surface and surrounds the exposure opening 58, and hooking walls 62 and groove portions 64 formed above the bases of the first and second ports 24 and 26 on the outside of the disposition portion 60. The disposition portion 60 is disposed with the support 34 and the hooking wall 62 is engaged with an engagement pawl 66 of the cap 32.

The exposure opening 58 has a diameter larger than the width of the internal flow channel 52, and the internal flow channel 52 is extended so as to indent the center of the exposure opening 58 into a groove shape. Stopper portions 59 inclined at a predetermined angle are formed between the rim of the exposure opening 58 and a pair of side walls 52a and 52a constituting the internal flow channel 52. When the male connector 100 is inserted into the third port 28, the stopper portions 59 restrict elastic deformation of the valve 36 by a predetermined extent or more, so that the stopper portions 59 function to prevent the male connector 100 from penetrating a slit 86 of the valve 36.

The third port 28 is a connection terminal including the cap 32, the support 34, and the valve 36, as described above. The third port 28 is fixedly connected to the mounting portion 56 such that it is perpendicular to the axial direction of the first and second ports 24 and 26. The connector 10 according to an exemplary embodiment of the disclosure is thus configured as a T-shaped port connector in which the third port 28 has a branching angle of 90° with respect to the main line flow channel 50. The male connector 100 (insertion body) of the third tube 12c is connected to the third port 28.

As illustrated in FIGS. 2 and 4, the cap 32 internally stores the valve 36, and has an external shape formed to be connected to the male connector 100 of the third tube 12c. The cap 32 includes a flange portion 68 on the lower end connected to the connector base portion 42 and a terminal portion 70 extending by a predetermined length upward from the flange portion 68.

The flange portion 68 has an outer diameter configured to cover the disposition portion 60 of the connector base portion 42. A pair of engagement pawls 66 projecting radially outward is provided at predetermined symmetrical positions of the peripheral edge of the flange portion 68. The pair of engagement pawls 66 is formed into a hook shape to have an interval slightly shorter than the interval between the pair of hooking walls 62 such that the pair of engagement pawls 66 fitted into the groove portions 64 of the connector base portion 42 hook onto the hooking wall 62.

The terminal portion 70 is formed into a cylindrical shape having a diameter smaller than that of the flange portion 68 and has an interior defining a hole portion 72 along the axial direction (vertical direction). The hole portion 72 has an upper side formed with an opening portion 40 narrowing radially inward, and under the opening portion 40, a storage portion 74 is provided which is formed to have a diameter larger than that of the opening portion 40 and which stores (receives) the support 34 and the valve 36.

The opening portion 40 is surrounded by a ring-shaped projection portion 70a projecting downward from the upper edge of the terminal portion 70 to have a predetermined inner diameter (inner diameter into which the valve 36 can be inserted). Further, the terminal portion 70 has an outer peripheral surface formed with a helical projection line 70b configured to threadedly engage a luer lock male connector.

The second line of the infusion set 14, including the male connector 100 of the third tube 12c connected to the connector 10, will be described with reference to FIG. 4. The male connector 100 employs, for example, an ISO standardized slip luer male connector. Specifically, the male connector 100 has an insertion cylinder 102 inserted into the connector 10 (cap 32).

The insertion cylinder 102 extends linearly axially, and has an end part (lower end part in FIG. 4) configured to press and open the slit 86 of the valve 36, when connected with the connector 10. A flow path 104 for the flow of a second infusion solution supplied from the third tube 12c is formed in the insertion cylinder 102. That is, the flow path 104 is configured as a flow channel of the second line (hereinafter, referred to as second line flow channel 110).

The insertion cylinder 102 has an outer peripheral surface formed into a tapered surface 102a having a diameter reducing toward the end. That is, the insertion cylinder 102 has a barrel portion having an outer diameter matching the inner diameter of the opening portion 40 of the cap 32 at a position of the insertion cylinder 102 inserted into the connector 10 by a predetermined amount, and the end part has an outer diameter formed slightly smaller than that of the barrel portion. The tapered surface 102a is fitted into the opening portion 40 as the insertion cylinder 102 is inserted into the connector 10 so that the insertion cylinder 102 is connected to the third port 28 (cap 32, support 34, and valve 36).

It will be understood by one skilled in the art that the male connector connected to the third port 28 is not limited to the slip luer male connector 100. For example, as illustrated by a dashed line in FIG. 4, a luer lock male connector 100A may be employed in which a connection cylinder 106 configured to surround the insertion cylinder 102 is provided, and a helical projection 108 provided on the inner peripheral surface of the connection cylinder 106 is threadedly engaged with the projection line 70b of the cap 32.

The support 34 of the third port 28 functions to support the valve 36 at a position apart from the internal flow channel 52 by a predetermined distance. That is, a space portion large enough to receive the male connector 100 (insertion cylinder 102) inserted by a predetermined amount or more is required in order to connect the third port 28 and the male connector 100. The support 34 has an upper part supporting the valve 36 and a vertically extending through hole 76 forming the space portion.

The support 34 includes a brim portion 78 disposed at the disposition portion 60 of the connector base portion 42, and a support cylinder 80 projecting upward from the upper surface of the brim portion 78. The support cylinder 80 has an upper part formed as a holding portion 82 and having an outer diameter smaller than that of the barrel portion of the insertion cylinder 102, and the holding portion 82 has an exterior surface engaged with a fixed portion 84 of the valve 36.

The through hole 76 is formed to penetrate the brim portion 78 and the support cylinder 80. The through hole 76 communicates with the exposure opening 58 while the support 34 is disposed at the disposition portion 60. The through hole 76 is configured as a flow channel in the third port 28, and allows the second infusion solution to flow from the second (another) line flow channel 110 to the main line flow channel 50. That is, a flow channel 38a in the main body 38 includes the first and second port flow channels 44 and 48, the internal flow channel 52, and the through hole 76. The valve 36 elastically deforms as the insertion cylinder 102 is inserted into the through hole 76. The through hole 76 and the opening portion 40 are thus configured as a space into which displacement of the valve 36 is permitted.

The valve 36 of the third port 28 is molded from an elastic material, different from the material of the other members, and has an elasticity for elastic deformation upon insertion of the male connector 100. The elastic material of the valve 36 is not particularly limited, but includes, for example, a synthetic rubber including polybutadiene, nitrile, chloroprene, or the like, natural rubber including polyisoprene or the like, a thermoset elastomer such as urethane rubber, silicon rubber, fluoro-rubber, a thermoplastic elastomer, or another elastomer.

The valve 36 includes the slit 86 at the center thereof which opens and closes based on the insertion and removal of the male connector 100. The value 36 functions to connect and block the second line flow channel 110 by opening and closing the slit 86. The valve 36 is formed into a disk shape having a relatively large film thickness, and includes an outside fixed portion 84 held between the cap 32 and the support 34, and an inside deformable portion 88 continuously disposed within the fixed portion 84. The deformable portion 88 has an upper part formed with an upper protruding portion 88a inserted into the opening portion 40.

The slit 86 is formed to vertically extend through the deformable portion 88, and is closed while the upper protruding portion 88a is stored in the opening portion 40 (not elastically deformed). The slit 86 is gradually opened by displacement of the deformable portion 88 (elastically deformed) relative to the fixed portion 84 as the male connector 100 is pressed into the through hole 76.

When the male connector 100 is not inserted into the third port 28, the through hole 76 under the deformable portion 88 defines a cavity, and the cavity causes trapped fluid, such as, entrapment of air before priming or the first infusion solution flowing through the main line flow channel 50 to accumulate in the through hole 76. Therefore, the connector 10 includes the guide wall portion 54 on the internal flow channel 52 to guide the first infusion solution flowing from the first port flow channel 44 toward the through hole 76 and thereby drain the trapped fluid. Configurations of the internal flow channel 52 and the guide wall portion 54 will be described below in detail.

As illustrated in FIG. 3 and FIGS. 5A to 5C, the internal flow channel 52 is formed to have a substantially square cross-sectional shape and to extend axially. The internal flow channel 52 is connected to the first and second port flow channels 44 and 48, each having a circular cross-sectional shape which extends into the connector base portion 42. The internal flow channel 52 has an upper side opened by the exposure opening 58. The internal flow channel 52 includes the pair of side walls 52a and 52a extending along the axial direction, a bottom wall 52b, and end walls 52c and 52c at both axial ends, defined as a boundary between the first and second port flow channels 44 and 48 and the internal flow channel 52. The end walls 52c of the internal flow channel 52 have areas larger than the cross-sectional areas of the first and second port flow channels 44 and 48, and have center portions formed (bored) for communication with the first and second port flow channels 44 and 48.

The guide wall portion 54 is formed to axially divide the internal flow channel 52 (i.e., upstream and downstream). The guide wall portion 54 is configured by a thickly formed protruding portion 90 extending from the axial center of the internal flow channel 52 toward the first port 24. The protruding portion 90 continuously extends from the pair of side walls 52a and 52a and the bottom wall 52b which constitute the internal flow channel 52. Further, the protruding portion 90 projects upward from the bottom wall 52b to a height above the bore positions of the first and second port flow channels 44 and 48. The stopper portions 59 have a center bottom part formed to be connected to the upper surface of the protruding portion 90.

Figure 5A:
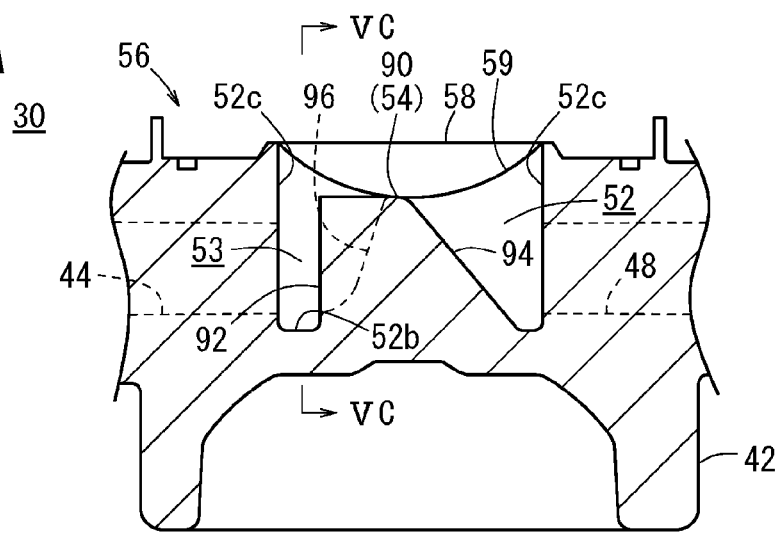
FIG. 5A is a cross-sectional view of the housing taken along the line VA-VA of FIG. 3.
Figure 5B:
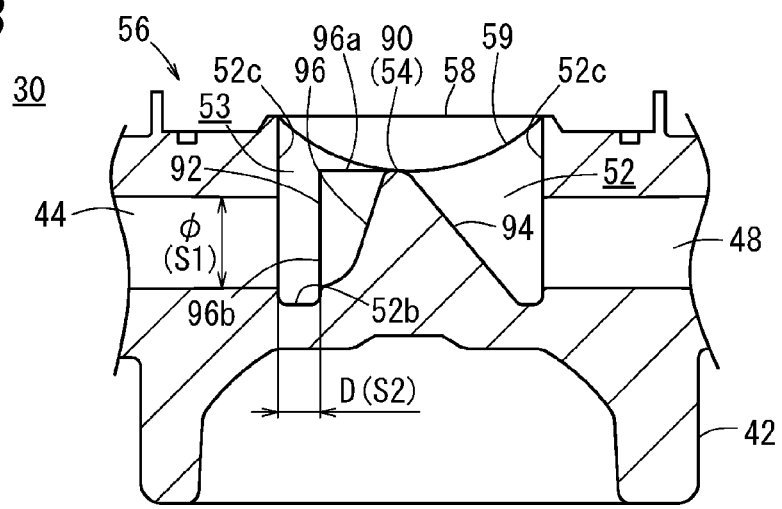
FIG. 5B is a cross-sectional view of the housing taken along the line VB-VB of FIG. 3.
Figure 5C:
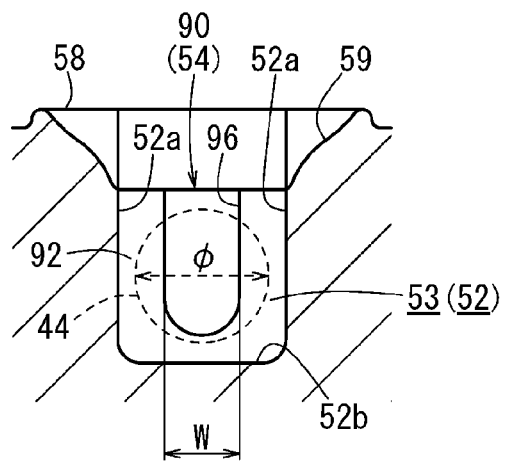
FIG. 5C is a cross-sectional view of the housing taken along the line VC-VC of FIG. 5A.

In the protruding portion 90, an upstream side wall surface 92 configured to guide the first infusion solution flowing from the first port flow channel 44 to the through hole 76 is formed on the first port flow channel 44 side, and a downstream side wall surface 94 configured to guide the first infusion solution or the trapped fluid flowing into the through hole 76 to the second port flow channel 48 is formed on the second port flow channel 48 side. Further, the upstream side wall surface 92 is formed with a notched groove 96 (notched portion) obtained by notching the widthwise center of the upstream side wall surface 92 upward, as best shown in FIG. 5c.

The upstream side wall surface 92 is disposed near the boundary (end wall 52c) between the first port flow channel 44 and the internal flow channel 52. The upstream side wall surface 92 is formed flat to surround the notched groove 96 and is perpendicular to the axis of the first port flow channel 44. Accordingly, a communication path between the internal flow channel 52 and the first port flow channel 44 is defined by an inflow space 53 including the pair of side walls 52a and 52a, the bottom wall 52b, the end wall 52c, and the upstream side wall surface 92. The inflow space 53 has a sufficiently small volume.

The inflow space 53 is a flow channel for the first infusion solution, interposed between the first port flow channel 44 and the through hole 76. The cross-sectional area S2 of the inflow space 53 is smaller than the cross-sectional area S1 of the first port flow channel 44 so that the inflow space 53 allows the first infusion solution to flow swiftly to the through hole 76. That is, the upstream side wall surface 92 of the protruding portion 90 is raised in the vicinity of the end wall 52c so that the cross-sectional area S2 of the inflow space 53 is sufficiently reduced. In particular, the upstream side wall surface 92 has an upper side projecting higher than a height of the first port flow channel 44 to face the end wall 52c, and the cross-sectional area S2 of the inflow space 53 near the through hole 76 is reduced.

The ratio between the cross-sectional area S1 of the first port flow channel 44 and the cross-sectional area S2 of the inflow space 53 is not particularly limited, but for example the ratio of the cross-sectional area S2 to the cross-sectional area S1 is preferably set to 75% or less. For example, when the connector 10 includes the first port flow channel 44 having an inner diameter φ (diameter) of 2 mm, the interval (distance) D between the end wall 52c and the upstream side wall surface 92 is set to approximately 0.8 mm. In this setting, the cross-sectional area S1 of the first port flow channel 44 is 3 mm² or more and the cross-sectional area S2 of the inflow space 53 is approximately 2 mm². Such a relationship is established so that the flow speed of the first infusion solution flowing into the inflow space 53 from the first port flow channel 44 is sufficiently increased without being blocked and the momentum of the first infusion solution conducted into the through hole 76 from the inflow space 53 is thereby considerably increased.

The notched groove 96 has an upper side formed by the protruding portion 90 at the axial center of the internal flow channel 52 in a side view (see FIG. 5B), and is connected to the lower part of the upstream side wall surface 92 so as to have a smooth curve extending from the upper surface of the protruding portion 90. That is, the notched groove 96 has an opening 96a on the upper surface of the protruding portion 90 and an opening 96b on the upstream side wall surface 92. The notched groove 96 conducts the first infusion solution flowing into the inflow space 53 into the flow path 104 of the insertion cylinder 102 while the connector 10 and the male connector 100 are connected to each other.

The notched groove 96 connected to the upstream side wall surface 92 preferably has a width W appropriately set in consideration of the size of the connector 10, the flow rate of the first infusion solution, or the like, and specifically, the width W is preferably smaller than an opening (inner diameter φ) of the first port flow channel 44 (see FIG. 5C). Therefore, the cross-sectional area of the notched groove 96 is reduced, and when the connector 10 and the male connector 100 are not connected, part of the first infusion solution flowing into the inflow space 53 from the first port flow channel 44 is directed to the notched groove 96, but has a flow speed increased along the notched groove 96. The rest of the first infusion solution has a flow speed increased by the inflow space 53 (upstream side wall surface 92). Therefore, the first infusion solution is swiftly guided to the through hole 76.

Further, when a first infusion solution having a high viscosity flows in the connector 10, the first infusion solution flows at a speed increased along the central axis of the first port flow channel 44 and reduced along the inner surface thereof. However, when the first infusion solution flowing along the inner surface of the first port flow channel 44 flows into the inflow space 53, the first infusion solution faces (collides with) the upstream side wall surface 92, and the flow speed of the first infusion solution is readily increased by the reduced cross-sectional area S2 of the inflow space 53.

The downstream side wall surface 94 of the protruding portion 90 is provided on the opposite side to the upstream side wall surface 92. The downstream side wall surface 94 is formed into a tapered shape and smoothly guides the first or second infusion solution flowing from the through hole 76 or the flow path 104 of the insertion cylinder 102 to the second port flow channel 48. It should be understood that the shape of the downstream side wall surface 94 is not especially limited, and may be formed as, for example, a wall surface perpendicular to the axis of the second port flow channel 48.

The connector 10 according to an exemplary embodiment of the disclosure is basically configured as described above. The functions and effects thereof will be described below. First, the connector 10 connected only with the first and second tubes 12a and 12b, that is, without connection with the third tube 12c, will be described in detail with reference to FIG. 4.

In the connector 10, the first tube 12a is connected to the first port 24, the second tube 12b is connected to the second port 26, and the third port 28 is closed by the valve 36. Therefore, the through hole 76 in the third port 28 has a large volume in the space portion under the valve 36.

The first infusion solution flowing through the main line flows into the first port 24 from the first tube 12a. The first infusion solution linearly moves in the connector base portion 42 through the first port flow channel 44, and flows into the inflow space 53 on the upstream side of the internal flow channel 52. The movement of the first infusion solution is guided upward (toward third port 28) by the upstream side wall surface 92 raised on the internal flow channel 52.

As described above, the cross-sectional area S2 of the inflow space 53 is formed smaller than the cross-sectional area S1 of the first port flow channel 44. Therefore, the flow speed of the first infusion solution flowing into the inflow space 53 from the first port flow channel 44 is increased in the inflow space 53. As a result, the first infusion solution swiftly flows toward the through hole 76 from the inflow space 53, and causes the fluid (including first infusion solution and trapped fluid) in the through hole 76 to flow largely (fluid turbulence) as a whole.

More specifically, the first infusion solution swiftly flowing into the through hole 76 flows uniformly in the through hole 76 and promotes agitation of the fluid in the through hole 76. Therefore, even if the trapped fluid exists in the through hole 76, the trapped fluid is agitated and easily mixed with the first infusion solution. The first infusion solution including the trapped fluid is moved downstream of the internal flow channel 52 beyond the protruding portion 90 from the through hole 76. Therefore, the trapped fluid is readily drained from the through hole 76.

The first infusion solution moved from the through hole 76 to the internal flow channel 52 smoothly flows to the second port flow channel 48 along the downstream side wall surface 94 being inclined. The first infusion solution is supplied into the second tube 12b through the second port flow channel 48, and administered to the patient from the second tube 12b.

Figure 6:
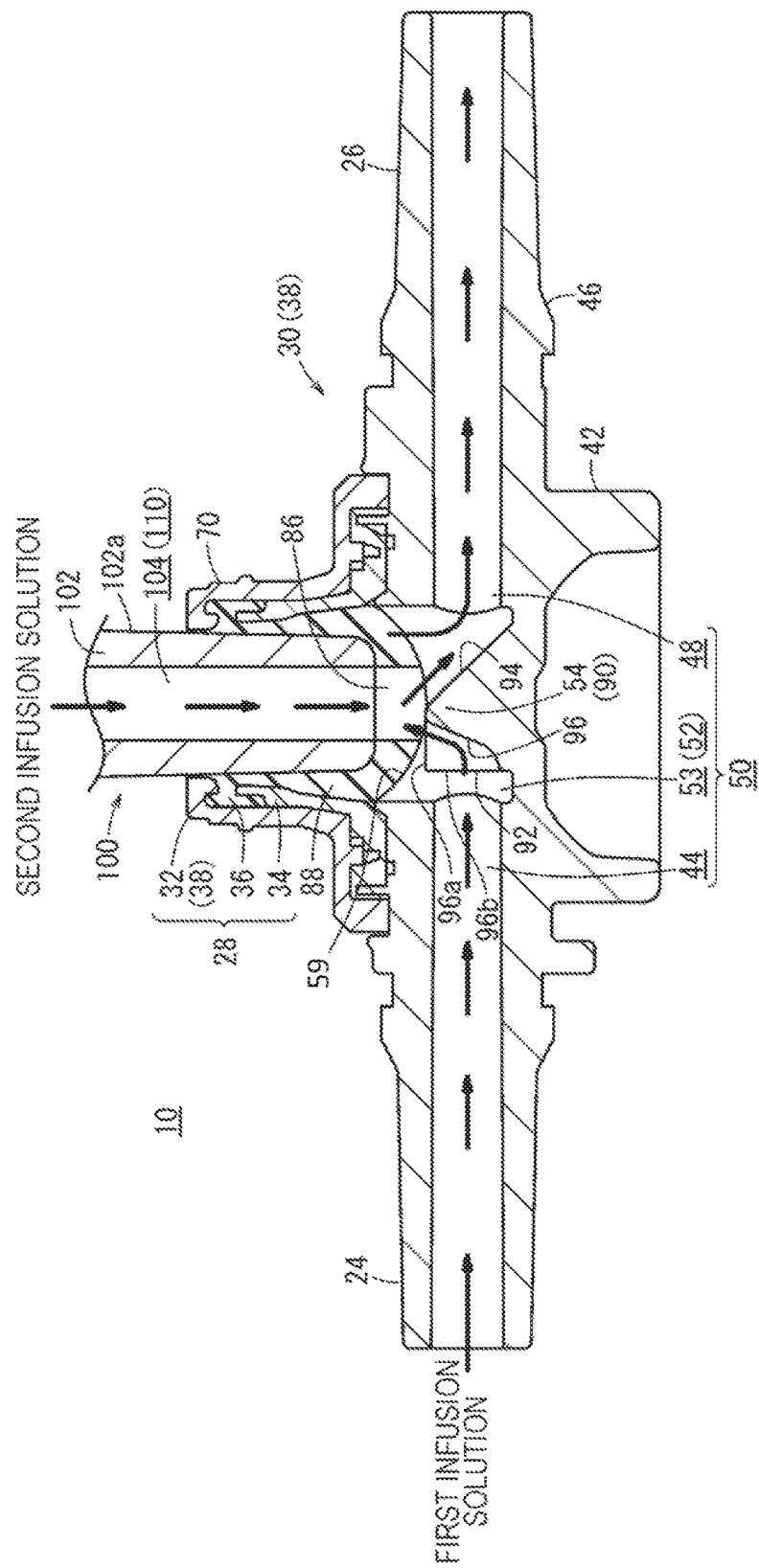
FIG. 6 is a side cross-sectional view illustrating a connected state of the male connector in the connector of FIG. 2.

Next, the connector 10 connected with the first to third tubes 12a to 12c will be described in detail with reference to FIG. 6. While the third port 28 and the male connector 100 are connected to each other, the insertion cylinder 102 presses the deformable portion 88 of the valve 36 to the lower side of the through hole 76. Therefore, the deformable portion 88 is elastically deformed (displaced) until restricted by the stopper portions 59 above the protruding portion 90. Therefore, the bottom surface of the deformable portion 88 is displaced to a position in the vicinity of the protruding portion 90 and the upper part of the inflow space 53 is substantially closed by the deformable portion 88. The slit 86 formed in the deformable portion 88 is opened at the axial center of the internal flow channel 52 by the elastic deformation of the deformable portion 88.

Since the notched groove 96 is disposed at the axial center of the protruding portion 90, the opening 96a on the upper surface side of the notched groove 96 partially overlaps with (faces) the slit 86. Therefore, the first infusion solution flowing into the inflow space 53 from the first port flow channel 44 enters the notched groove 96 from the opening 96b of the upstream side wall surface 92, and flows into the flow path 104 of the insertion cylinder 102 along the notched groove 96. In this case, since the notched groove 96 is formed to have a width smaller than that of the first port flow channel 44, the flow speed of the first infusion solution is increased, and the first infusion solution swiftly flows into the flow path 104.

The second infusion solution is supplied to the flow path 104 through the third tube 12c such that the first infusion solution and the second infusion solution are readily joined (mixed) in the flow path 104. The mixed first and second infusion solution flows downstream of the internal flow channel 52 from the flow path 104 based on the flow of the fluid, is smoothly guided to the second port flow channel 48 along the downstream side wall surface 94, and is further administered to the patient through the second tube 12b.

As described above, according to the connector 10 of the exemplary embodiment, the upstream side wall surface 92 is provided to reduce the cross-sectional area S2 near the through hole 76 relative to the cross-sectional area S1 of the first port flow channel 44 so that the momentum of the first infusion solution directed from the inflow space 53 having the reduced cross-sectional area S2 to the through hole 76 can be increased. Therefore, in the through hole 76, the first infusion solution having the increased momentum can promote the flow of fluid, and the trapped fluid can be readily drained from the through hole 76. Therefore, the connector 10 can considerably increase the safety of infusion, and the infusion solution can be reliably administered to the patient.

In this configuration, the upstream side wall surface 92 faces the first port flow channel 44, so that the inflow space 53 having a reduced cross-sectional area can be readily formed on the internal flow channel 52 without considerably changing the internal shape or the like of the connector 10 (internal flow channel 52). The upstream side wall surface 92 faces substantially perpendicularly to the axial direction of the first port flow channel 44, so that the upstream side wall surface 92 can be disposed near the first port flow channel 44 and the first infusion solution flowing out of the first port flow channel 44 can be readily conducted to the through hole 76.

The connector 10 has the notched groove 96 connected to the upstream side wall surface 92 and disposed at the axial center of the internal flow channel 52 so that, even when the inflow space 53 is formed by the upstream side wall surface 92, the second line flow channel 110 of the male connector 100 and the main line flow channel 50 (internal flow channel 52) are readily communicated with each other through the notched groove 96. Therefore, even when the male connector 100 is connected to the connector 10, the first infusion solution flowing from the first port 24 can smoothly flow to the second port 26.

Further, when the male connector 100 is connected to the third part 28 and the valve 36 is displaced, the upstream side wall surface 92 extends from the bottom wall 52b of the internal flow channel 52 to the vicinity of the bottom surface of the valve 36 displaced through the through hole 76, such that the inflow space 53 is practically closed by the valve 36. Therefore, the first infusion solution flowing into the inflow space 53 has a flow speed increased by the notched groove 96 and is smoothly conducted to the flow path 104.

Figure 7:
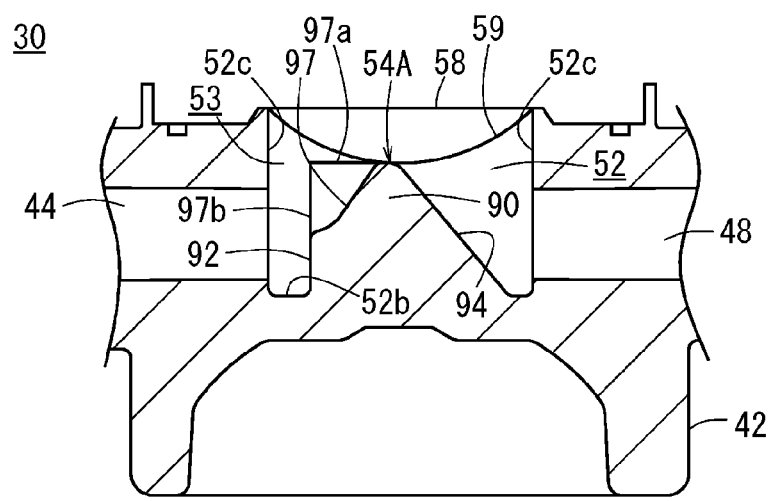
FIG. 7 is a side cross-sectional view illustrating a housing of a connector according to a further exemplary embodiment of the disclosure.

It should be understood that the guide wall portion 54 provided in the connector 10 according to the above exemplary embodiment is not limited to the above-mentioned configuration, but various configurations can be employed. For example, as illustrated in FIG. 7, a guide wall 54A may have a notched groove 97 formed at the protruding portion 90 to have a depth smaller than that of the notched groove 96 according to the previous exemplary embodiment. That is, an opening 97a in the notched groove 97 on the upper surface side of the protruding portion 90 is formed at the same position as the opening 96a according to the previous exemplary embodiment, but an opening 97b in the notched groove 97 formed in the upstream side wall surface 92 is notched to substantially an intermediate part of the upstream side wall surface 92 in a height direction. Accordingly, the upstream side wall surface 92 has a large flat portion such that it favorably receives the first infusion solution flowing from the first port flow channel 44 and allows upflow of the first infusion solution. Therefore, the first infusion solution flowing into the inflow space 53 can be swiftly conducted to the through hole 76.

The detailed description above describes a connector. The disclosure is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A connector comprising:
   a main body including a housing and a cap;
   a first port, a second port and a third port provided at the main body, the first port, the second port and the third port each having a flow channel allowing inflow or outflow of fluid;
   an internal flow channel provided in the main body, the internal flow channel configured to communicate between the flow channel of the first port and the flow channel of the second port;
   a space portion provided in the third port and connected in fluid communication with the internal flow channel; and
   a protruding portion extending from an axial center of the internal flow channel toward the third port, the protruding portion being integral with the housing;
   wherein the protruding portion includes a wall surface provided in the internal flow channel, the wall surface facing the flow channel of the first port, and the wall surface being spaced from an end wall of the housing which defines a boundary between the flow channel of the first port and the internal flow channel such that the wall surface is configured to guide fluid flowing into the internal flow channel from the first port to the space portion;
   wherein the wall surface reduces a cross-sectional area of a flow channel for fluid near the space portion relative to a cross-sectional area of the flow channel of the first port;
   wherein the wall surface includes a notched portion positioned along an axial center of the internal flow channel, the notched portion including an opening in an upper surface of the protruding portion and an opening in the wall surface.

2. The connector according to claim 1, wherein the wall surface faces substantially perpendicularly to an axial direction of the flow channel of the first port.

3. The connector according to claim 2, wherein the protruding portion further includes a downstream side wall surface facing the flow channel of the second port, and the downstream side wall surface is connected from an upper part of the wall surface and inclined toward a bottom surface of the flow channel of the second port.

4. The connector according to claim 1, wherein the wall surface has an upper part projecting above a height of the flow channel of the first port.

5. The connector according to claim 1, wherein the third port is perpendicular to an axial direction of the first port and the second port.

6. The connector according to claim 1, wherein the third port include an elastically deformable valve.

7. The connector according to claim 6, wherein the valve is configured to open when a connector portion is inserted into the third port.

8. The connector according to claim 1, wherein a ratio between the cross-sectional are of the flow channel of the first port and the cross-sectional area of the flow channel near the space portion is 75% or less.

9. The connector according to claim 1, wherein the notched portion has a width smaller than an inner diameter of the flow channel of the first port.

10. An infusion set comprising:
    a connector according to claim 1;
    a first tube connected to the first port of the connector and configured to allow a first infusion solution to flow from the first tube through the first port to the internal flow channel;
    a second tube connected to the second port of the connector and configured to allow the first infusion solution to flow from the internal flow channel through the second port and the second tube;
    wherein the wall surface is configured to increase a flow rate of the first infusion solution flowing from the first port to the internal flow channel.

11. The infusion set according to claim 10, wherein the wall surface faces substantially perpendicularly to an axial direction of the flow channel of the first port.

12. The infusion set according to claim 10, wherein the third port is perpendicular to an axial direction of the first port and the second port.

13. The infusion set according to claim 10, further comprising a third tube connected to the third port and configured to allow a second infusion solution to flow from the third tube through the third port to the internal flow channel.

14. The infusion set according to claim 13, wherein the third port includes an elastically deformable valve.

15. The infusion set according to claim 14, wherein the third tube includes a connection portion for opening the valve when the third tube is connected to the third port.

* * * * *